US012765798B2

(12) United States Patent
Rapert et al.

(10) Patent No.: US 12,765,798 B2
(45) Date of Patent: Oct. 20, 2026

(54) DEVELOPMENT OF A SIMPLE, LOW-COST METHOD OF MEASURING AMMONIA CONCENTRATION IN EXHALED BREATH FOR ROUTINE MONITORING OF CHRONIC KIDNEY DISEASE

(71) Applicant: Clemson University Research Foundation, Clemson, SC (US)

(72) Inventors: Riley Rapert, Clemson, SC (US); Robert A. Latour, Clemson, SC (US); George Chumanov, Clemson, SC (US); Tyler George Harvey, Clemson, SC (US); Guzeliya Korneva, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 578 days.

(21) Appl. No.: 17/517,919

(22) Filed: Nov. 3, 2021

(65) Prior Publication Data

US 2023/0133069 A1 May 4, 2023

(51) Int. Cl.
*A61B 5/097* (2006.01)
*A61B 5/08* (2006.01)

(52) U.S. Cl.
CPC .............. *A61B 5/082* (2013.01); *A61B 5/097* (2013.01)

(58) Field of Classification Search
None
See application file for complete search history.

(56) References Cited

U.S. PATENT DOCUMENTS

2002/0026937 A1 * 3/2002 Mault .................. A61B 5/1112 128/200.24
2003/0023182 A1 * 1/2003 Mault .................... A61B 5/083 600/532
2003/0028120 A1 * 2/2003 Mault ................. G01N 33/497 600/531

(Continued)

FOREIGN PATENT DOCUMENTS

WO WO-2021089992 A1 * 5/2021 ............ A61B 5/082

OTHER PUBLICATIONS

Chan et al. Breath Ammonia Is a Useful Biomarker Predicting Kidney Function in Chronic Kidney Disease Patients. Biomedicines 2020; 8:468. doi: 10.3390/biomedicines8110468.

(Continued)

*Primary Examiner* — Charles A Marmor, II
(74) *Attorney, Agent, or Firm* — Fredrikson & Byron, P.A.

(57) ABSTRACT

An apparatus for measuring the ammonia concentration in exhaled breath and a method for measuring the ammonia concentration in exhaled breath. The apparatus comprises a sample collection portion, capable of capturing exhaled breath to control the volume of exhaled breath, a pressure gauge for the control of the flow rate of exhaled breath, a small diameter inner tube oriented in a perpendicular direction to the colorimetric sensor to focus the exhaled breath stream onto the central region of the sensor, and an analysis portion capable of receiving the exhaled breath from the sample collection portion. The analysis portion comprises a colorimetric sensor comprising an active component on a substrate. The colorimetric sensor changes color proportional to the ammonia concentration in the exhaled breath.

13 Claims, 7 Drawing Sheets

(56) References Cited

U.S. PATENT DOCUMENTS

| | | | | |
|---|---|---|---|---|
| 2004/0077965 | A1* | 4/2004 | Hubbard | A61B 5/083<br>73/23.3 |
| 2005/0171449 | A1* | 8/2005 | Suslick | G01N 21/272<br>436/164 |
| 2012/0165693 | A1* | 6/2012 | Williams | A61B 5/082<br>600/532 |

OTHER PUBLICATIONS

Chen et al. Correlation between breath ammonia and blood urea nitrogen levels in chronic kidney disease and dialysis patients. Journal of Breath Research 2020; 14:036002. doi: 10.1088/1752-7163/ab728b.

Wallace MAG, Pleil JD. Evolution of clinical & environ. health applications of exhaled breath research: . . . Analytica Chimica Acta. 2018; 1024:18-38. doi: 10.1016/j.aca.2018.01.

King et al. Isoprene and acetone concentration profiles during exercise on an ergometer. J. Breath Res. 2009; 3:027006. doi: 10.1088/1752-7155/3/2/027006.

King et al. A mathematical model for breath gas analysis of volatile organic compounds with special emphasis on acetone. J. Math. Biol. 2011; 63:959-999.

King et al. Dynamic profiles of volatile organic compounds in exhaled breath as determined by a coupled PTR-MS/GC-MS study. Physiol. Meas. 2010; 31:1169-1184.

Martina et al. The Effectiveness of Acetone Breath Content Using Chitosan Based Sensor in Patients Diabetes Mellitus. Maced J. Med Sci. 2019; 7(20):3391-3394.

Wang et al. Exhaled volatile organic compounds as lung cancer biomarkers during one-lung ventilation. Sci. Rep. 2014; 4:7312. doi: 10.1038/srep07312.

Narasimhan LR, Goodman W, Patel CK. Correlation of breath ammonia with blood urea nitrogen & creatinine during hemodialysis. Proceedings/National Acad. of Sciences 2001.

Courbat et al. Evaluation of pH indicator-based colorimetric films for ammonia detection using optical waveguides. Sensors and Actuators B 2009; 143: 62-70.

Hibbard T, Killard AJ. Breath ammonia levels in a normal human population study as determined by photoacoustic laser spectroscopy Journal of Breath Research. 2011.

Solga SF, Mudalel ML, Spacek LA, Risby TH. Fast and accurate exhaled breath ammonia measurement. J Vis Exp. 2014;(88):51658.

Paredi et al., "Exhaled Ethane, a Marker of Lipid Peroxidation, Is Elevated in Chronic Obstructive Pulmonary Disease" , Am J Respir Crit Care Med, vol. 162, Jan. 14, 2000, pp. 369-373.

Obermeier et al., "Exhaled Volatile Substances Mirror Clinical Conditions in Pediatric Chronic Kidney Disease", PLOS One, 12(6), Jun. 1, 2017, pp. 18.

Sepehr et al., "A Sensitive Determination of Ammonia and Nitrite in Exhaled Breath Condensate of Healthy Humans by Using Berthelot Reaction", Current Pharmaceutical Analysis, vol. 14, Sep. 6, 2017, pp. 555-561.

Ishida et al., "Real-time breath ammonia measurement using a novel cuprous bromide sensor device in patients with chronic liver disease: a feasibility and pilot study", Journal of Breath Research, vol. 15, Feb. 7, 2020, pp. 11.

* cited by examiner

DEVELOPMENT OF A SIMPLE, LOW-COST METHOD OF MEASURING AMMONIA CONCENTRATION IN EXHALED BREATH FOR ROUTINE MONITORING OF CHRONIC KIDNEY DISEASE

FIELD OF THE INVENTION

The present invention is related to an apparatus for measuring ammonia concentration in the exhaled breath for the determination and monitoring of chronic kidney disease.

BACKGROUND

Chronic kidney disease (CKD), a condition in which a patient's kidneys fail to effectively filter their blood, is estimated to affect more than one in seven American adults. It places one of the largest burdens on the healthcare system costing Medicare over $120 billion in 2017 alone. Commonly called the "silent disease," CKD presents with no symptoms in its early stages; therefore, most patients are diagnosed at an advanced stage leading to poor prognosis. Hemodialysis or kidney transplantation are the best treatments for the most advanced stage of kidney disease known as end-stage renal failure (ESRF). However, due to the high costs and inconvenience of hemodialysis and a lack of available kidneys for transplant, mortality rates remain high for those with ESRF. Therefore, better management of chronic kidney disease in its earlier stages is the key to overcoming the disease.

Blood urea nitrogen (BUN) levels and glomerular filtration rates (GFR) are used as the criteria for diagnosing and staging chronic kidney diseases. Currently, blood and urine tests are necessary to obtain the measurements needed to monitor and manage kidney disease state progression. These tests require patient compliancy as they are performed in clinics where experienced personnel will collect and analyze the samples. Moreover, these sampling procedures are invasive, embarrassing, and can be inaccurate as they have increased chances of preanalytical errors and require a longer time before diagnosis. To resolve the faults of these techniques, new research has shifted to exploiting biomarkers other than blood and urine as a diagnostic aid.

Breath has emerged as an ideal solution to this problem due to its non-invasive nature and ability to take repeat measurements with minimal discomfort to the patient. While a plethora of new breath-analysis research has developed in the past twenty years, examining exhaled breath is an ancient practice. Even in the time of Hippocrates, doctors were "smelling" the breath of patients to diagnose diseases by linking a sweet odor with diabetes and a fishy odor with kidney-related diseases. Since 1971 when Linus Pauling discovered that exhaled breath is a complex gas containing at least 200 volatile organic compounds (VOCs), much work has been done to identify all components of exhaled breath, which is now known to contain more than 3,500 VOCs. The levels of VOCs present in exhaled breath change when a healthy individual enters a pathological state, and this change may be detected and utilized for diagnosis and monitoring of a disease. Therefore, breath analysis has great potential to provide a cost-effective, real-time, quantifiable, diagnostic point-of-care detection method.

In patients suffering from kidney disease, the elevated levels of the VOC ammonia are responsible for the fish-like odor in exhaled breath. Ammonia production results from metabolic processes in the body, primarily protein metabolism by gut bacteria. In a healthy individual, the liver converts this ammonia to urea, and the kidneys filter out the waste through the urine. However, when the kidneys fail to function properly, waste will accumulate in the bloodstream. Ammonia and urea convert reversibly, so urea waste accumulation results in higher systemic levels of ammonium ions in the bloodstream. The excess urea will also increase urea concentration in saliva where it is degraded into gaseous ammonia, and the excess ammonium ions in the blood stream also travel to the lung alveoli where they undergo gas exchange. Both fates result in the increased levels of gaseous ammonia detected in the patient's exhaled breath. Previous studies have documented the association between these increased ammonia concentrations and decreased kidney function. While a healthy individual will typically have an exhaled breath ammonia level in a range from 50 to 1,500 parts-per-billion (ppb), patients suffering from end-stage renal failure can have ammonia levels as high as 15,000 ppb. Therefore, ammonia levels in exhaled breath have the potential to be exploited to track disease-state progression of those suffering from chronic kidney disease.

Currently, there exist techniques such as gas chromatography mass spectrometry, selected-ion-flow-tube mass spectrometry, and laser-acoustic-based spectrometry, which can be utilized to determine VOC levels in exhaled breath. However, diagnostic devices that employ these techniques are bulky, costly, require experienced personnel, and are not suitable for at-home use. And while novel technologies comprised of nanotechnology or smart polymers have recently been explored, they currently do not have the ability to detect trace VOCs at the sensitivity needed for clinical application.

In spite of the advances, those of skill in the art still desire a simple, quick, and low-cost method for measuring ammonia concentration in exhaled breath, thereby leading to improved care and decreased morbidity rates.

SUMMARY OF THE INVENTION

It is an object of the invention to provide a simple, quick, and low-cost method, and device, for measuring ammonia concentration in exhaled breath.

A particular feature of the invention is the ability to provide a device which can be used without medical personnel thereby allowing a patient to monitor and track a disease, particularly CKD, associated with increased ammonia in exhaled breath.

A particular advantage is the ability to detect diseases associated with high ammonia levels in exhaled breath early thereby allowing for early medical intervention.

These and other advantages, as will be realized, are provided in an apparatus for measuring breath ammonia concentration in exhaled breath. The apparatus comprises a means to monitor breath flow rate, a sample collection portion, capable of capturing exhaled breath, and an analysis portion capable of responding to the concentration of ammonia in said exhaled breath from said breath sample. The analysis portion comprises a colorimetric sensor comprising an active component on a substrate. The colorimetric sensor changes colors proportional to breath ammonia concentration in said exhaled breath.

Yet another embodiment is provided in a method for determining breath ammonia in exhaled breath comprising:

providing an apparatus comprising:

a sample collection portion capable of capturing exhaled breath; and an analysis portion capable of responding to the concentration of ammonia in the exhaled breath wherein the analysis portion comprises a colorimetric sensor comprising an active component on a substrate wherein the colorimetric sensor changes color proportional to breath ammonia concentration in the exhaled breath;
calibrating the apparatus by passing a series of control gases simulating exhaled breath with known ammonia concentrations through the apparatus to determine a relationship between a control color change and the known ammonia concentrations;
having a patient exhale breath into the apparatus;
measuring a clinical color change; and
determining a breath ammonia concentration in said exhaled breath based on said relationship.

DESCRIPTION

The present invention is related to a simple, at-home method for patients to routinely track the breath ammonia levels in their exhaled breath. This is accomplished by a system capable of detecting gaseous ammonia in exhaled breath. More specifically, the present invention is related to an apparatus which a patient can exhale breath into wherein the exhaled breath is captured and the concentration of breath ammonia in the exhaled breath can be determined by colorimetric methods.

Provided herein is a non-invasive, exhaled breath-based test that provides the patient an indication of their health in real-time. The method is fast, user-friendly, and low-cost allowing patients to regularly track their breath ammonia levels from the comfort of their home thereby allowing a patient to assess their health more often and at a lower cost providing clinicians frequent assessment of their patients' levels to assist in making therapeutic decisions to help slow the progression of CKD or other diseases which cause a high breath ammonia concentration in exhaled breath.

Of particular importance is the ability for at-home monitoring for patients with chronic kidney disease (CKD). At-home monitoring of ammonia is also important for other conditions such as for individuals with the rare metabolic disorder known such as a urea cycle disorder (UCD), which can lead to critical life-threatening increases in ammonia concentration in the blood stream. Patients suffering from hepatic encephalopathy (HE) have also been shown to have increased levels of ammonia in their blood and these patients may benefit from the invention. Another particular feature is the ability to track progression of these diseases allowing patients to better manage their ammonia levels and reduce the risk of a life-threatening ammonia spike.

The invention will be described with reference to the figures which are integral, but non-limiting, part of the specification provided for clarity of the invention. Throughout the various figures similar elements will be numbered according.

Figure 1:
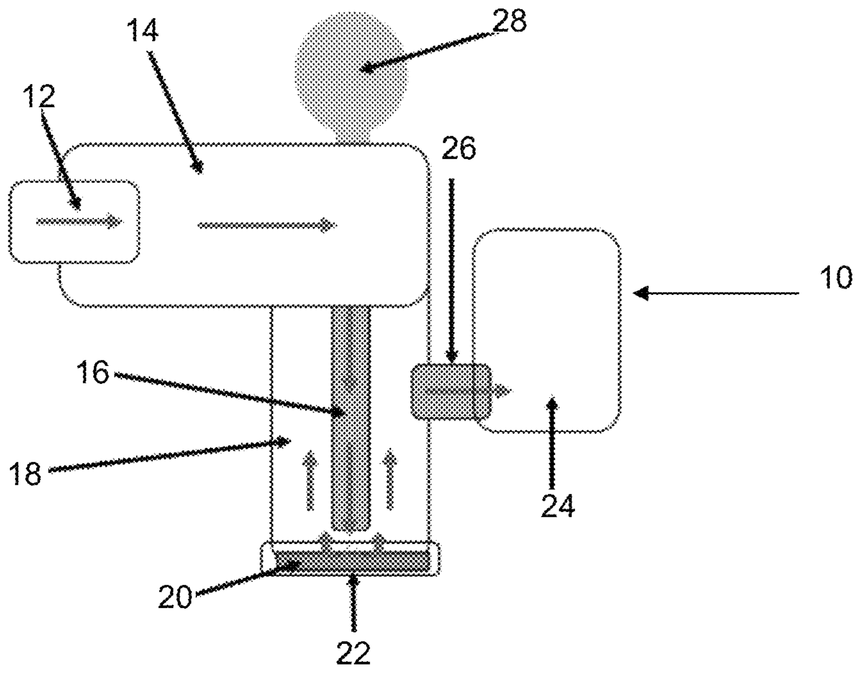
FIG. 1 is a schematic representation of an embodiment of the invention.

An embodiment of the invention is illustrated schematically in FIG. 1. In FIG. 1, the apparatus, 10, comprises a mouthpiece, 12, through which the exhaled breath, or sample, flows for capture. The mouthpiece preferably contains a check valve to only allow breath to flow in the direction from the patient into the device, and which is preferably attached to an inlet tube, 14, for the convenience of being able to disassembly and clean the apparatus. The diameter of the inlet tube, being larger than the diameter of the internal cylinder, causes droplets of saliva, potentially carried in the exhaled breath, to drop out of the flow stream and thus prevent their contact with the sensor's surface, which may cause irregular color spots on the sensor. The mouthpiece and inlet tube are taken together to represent a sample collection portion of the apparatus. The exhaled breath flows through a small-diameter internal cylinder, 16, which is within a column, 18, which focuses the stream of exhaled breath onto the center of a colorimetric sensor, 20, preferably contained in a bottom cap, 22. For the purposes of the invention functional contact between the exhaled breath and colorimetric sensor is defined as sufficient flow interaction for any breath ammonia in the exhaled breath to react with the active component of the colorimetric sensor. The colorimetric sensor, 20, is preferably contained in a donut, or annular-shaped holder, which is preferably a hydrophobic plastic to prevent condensation and to restrict the impingement of the exhaled breath to be focused on the central region of the colorimetric sensor. The internal cylinder, column, colorimetric sensor and optional holder are taken together to represent an analysis portion of the apparatus. The exhaled breath flows from the column to a sample bag, 24, preferably through a side arm, 26. The sample bag and side arm is taken together to represent a capture element of the apparatus that regulates the volume of breath that is exhaled through the device during a breath test. A pressure gauge, 28, allows the patient to be aware of the pressure in the system to ensure an adequate flow rate of breath is exhaled during the breath test. The various components are illustrated as being independent elements since this facilitates disassembly, cleaning and recharging with colorimetric sensors. Any combination of components can be combined, or listed components may be bifurcated, with the understanding that the exhaled breath being analyzed passes from the patient, through the colorimetric sensor and is either captured or expelled in a manner which inhibits the exhaled breath being returned to the patient.

The outlet of the internal cylinder is preferably placed approximately 5 mm (0.2") from the sensor such that the stream of exhaled breath impinges in a perpendicular direction onto the central region of the sensor by being press fit into the bottom of the inlet tube. This arrangement directs the gas sample to impede onto the exposed area of the sensor to achieve functional contact. Changing the distance from the end of the internal cylinder to the sensor can adjust the sensitivity of the apparatus.

The colorimetric sensor comprises an active component capable of changing color proportional to the amount of breath ammonia impinging on the colorimetric sensor wherein the active component is on a substrate. The active component of the colorimetric sensor is preferably selected from the group consisting of Bromocresol Green (BCG) preferred, Bromophenol Blue (BPB), Bromocresol Purple (BCP), Titanium(IV) Oxide, Berthelot's reagent, and Hydroquinone. Bromocresol Green (BCG) is preferred. Bromocresol Green (BCG) (ACS Regent, #114359-5G), Bromophenol Blue (BPB) (ACS Reagent, #114391-5G), Bromocresol Purple (BCP) (ACS Reagent, #B5880-5G), Titanium(IV) Oxide ($TiO_2$) (Nanopowder, 21 nm, #718467-100G), and Hydroquinone (Reagent plus, #H9003-100G) are all commercially available Sigma Aldrich. Bromophenol Blue is yellow in acid and turns blue in a pH range of 3.0-4.6. Bromocresol Purple is yellow in acid and turns purple in a pH range of 5.2-6.8. Bromocresol green is yellow in acid and turns green in a pH range of 3.8-5.4.

A particularly preferred colorimetric sensor comprises Bromocresol Green (BCG) Powder (ACS Regent, #114359-5G), methanol solution (Fisher Chemical, CAS 67-56-1), on a Whatman grade 3 MM cellulose chromatography paper substrate from a 25 mm diameter (Whatman, product #1030-025) are particularly suitable for demonstration of the invention. A housing unit comprising polycarbonate, polypropylene, and Teflon® components, a 1-L sampling bag, a pressure gauge, and a mouthpiece is also suitable for demonstration of the invention.

In an embodiment the internal cylinder can be made from a relatively hydrophobic polymer such as polypropylene with the donut, or annular, shaped holder made from a relatively hydrophobic polymer such as polytetrafluoroethylene. All other components can be made from polycarbonate. Sample volume can be controlled by the addition of a sample bag to collect the exhaled breath. A Tedlar sample bag which is at last 0.1 L to no more than 5 L is preferable with a 1-L Tedlar sample bag (Cole-Parmer, item #EW-86561-00) being particularly suitable for demonstration of the invention.

A pressure gauge is preferably used to demonstrate the invention thereby providing feedback regarding back pressure to the user during sampling to control the flowrate of the sample. A pressure gauge from Grainger, item #491064, is particularly suitable for demonstration of the invention.

A mouthpiece is preferably attached to the inlet tube of the housing unit. A particularly preferred mouthpiece comprises a one-way valve to trap the exhaled breath sample inside the unit and eliminates the chance of rebreathing the exhaled breath. A Carolina Diagnostic Solutions, item #SKU: 20980 mouthpiece is particularly suitable for demonstration of the invention.

In an exemplary embodiment colorimetric disc sensors can be formed from 50 mg of bromocresol green powder dissolved in 50 mL methanol solution referred to herein as BCG solution. To demonstrate the invention a 150 μL of BCG solution would be pipetted onto the middle of a 25 mm diameter Whatman 3 MM chromatography paper preferably laid flat on a plate made from a hydrophobic polymer such as polyethylene, polypropylene or polytetrafluoroethylene. This would be left to dry for about 30 minutes and then stored in a sealed package, such as a relatively thick plastic bag, to prevent exposure to ambient air prior to use.

The substrate is preferably selected from chromatography paper and particularly Whatman grade 3 MM cellulose chromatography paper.

The components are assembled to create the apparatus which a user can breathe into. The components can be assembled by press fitting the internal cylinder preferably about 0.2" (5 mm) into the bottom of the inlet tube. The column would then be placed around the internal cylinder and preferably screwed onto mating threads located on the bottom of the inlet tube. The side arm can be glued to the side of the column with aligned orifices such as the 0.375" (9.525 mm) holes. A colorimetric disc sensor is placed in the bottom cap and covered with a hydrophobic polymer, preferably polypropylene or polytetrafluoroethylene, donut or annular shaped holder. The bottom cap can then be screwed onto the bottom of the column such as with mating threads. This geometry leaves approximately 0.2" (5 mm) between the outlet of the internal cylinder and the colorimetric disc sensor, with the flow of exhaled breath directed to impinge on the central region of the sensor disc in a perpendicular direction. The pressure gauge can be screwed into the top of the inlet tube, and the mouthpiece can be press fit into the side of the inlet tube. The sampling bag can be press fit into the side arm.

EXPERIMENTAL

Calibration

It is preferable to calibrate the apparatus by providing a controlled amount of a control gas comprising a known amount of ammonia gas in a known volume of humidified carbon dioxide and air to mimic exhaled breath with $NH_3$ concentration from 0 to 12 ppm. Particularly preferred is a 5% $CO_2$-in-air gas cylinder which flows through a water bath, such as at 44° C. to humidify the $CO_2$-air stream to about 94% relative humidity, followed by the addition of an ammonia-in-air gas stream to the flowing $CO_2$-in-air into the apparatus. Mass flow controllers would be utilized as would be apparent to one of skill in the art. For the purposes of demonstration of the invention a 5% $CO_2$-in-air cylinder is suitable for use which can be purchased from Airgas (part #X02A195C2000117). The ammonia source can be purchased as 20-ppm or 30-ppm ammonia-in-air stock cylinders from Airgas (part #X02A199CP580081 and X02A199CP5837Q1, respectively). A regulator suitable for use with the ammonia cylinders is available commercially from Airgas (part #Y111226CC10-AL). Mass Flow Controllers from Cole-Parmer, referred to as Masterflex Proportional Flowmeter Controller, Mass, 10 L/min Gas (item #UX-32907-7)1 and 5 L/min Gas (item #HV-32907-69) are suitable for demonstration of the invention.

As would be realized, the sensor disc changes color in proportion to the ammonia concentration. The color change of a sensor disc after a test run can be analyzed by a quantifying color scale, such as RGB (red-green-blue) color with either control or accounting for ambient lighting conditions. For example, a sensor disc can be placed on a 2"×2" white plastic plate under an LED-lit enclosure, to control the lighting, and the disc can be photographed such as by a smartphone camera followed by RGB color analysis to quantify the color change. Alternatively, the color change could be simply determined by comparing it by eye against a set of standard color patches that are calibrated to known ammonia concentrations.

To prepare the gas flow system, 100 mL of DI water can be added to a 500 mL side-arm flask and placed in a water bath set to 44° C. The mass flow controllers can be connected to the gas cylinders with dry PVC tubing. The 5% $CO_2$-in-air gas line is preferably humidified by its introduction into the headspace of a sealed side arm flask filled with DI water placed in the water bath. The humidified air could exit out the side arm of the flask and combined with the ammonia-air stream to create the final desired concentration of gaseous ammonia. Dry PVC tubing is preferably used to connect the combined airflow system to the housing unit.

The system can be first flushed with dry 5% $CO_2$ in air for 15 seconds for calibration. A colorimetric disc sensor would be placed in the bottom cap of the housing unit, covered with the, preferably Teflon, holder, and the apparatus would be sealed. The exhaled breath collection bag, such as a 1-L Tedlar bag, would be attached to the side arm and its valve fitting would be opened.

For calibration purposes the mass flow controllers would be set as needed to obtain the desired $NH_3$ concentration such as at a combined total flowrate of 4 liters per minute (LPM) with an exemplary range of flow rates suitable for calibration provided in Table 1.

TABLE 1

| $NH_3$ Stock [ppm] | 20.5 | Flowrate [LPM] | 4 |
|---|---|---|---|
| $NH_3$ Target [ppm] | Dilution | $NH_3$ Flow [LPM] | Air Flow [LPM] |
| 0 | 0.000 | 0.000 | 4.000 |
| 1 | 0.049 | 0.195 | 3.805 |
| 2 | 0.098 | 0.390 | 3.610 |
| 3 | 0.146 | 0.585 | 3.415 |
| 4 | 0.195 | 0.780 | 3.220 |
| 5 | 0.244 | 0.976 | 3.024 |
| 6 | 0.293 | 1.171 | 2.829 |
| 8 | 0.390 | 1.561 | 2.439 |
| $NH_3$ Stock [ppm] | 30.8 | Flowrate [LPM] | 4 |
| $NH_3$ Target [ppm] | Dilution | $NH_3$ Flow [LPM] | Air Flow [LPM] |
| 10 | 0.325 | 1.299 | 2.701 |
| 12 | 0.390 | 1.558 | 2.442 |

After exposure of the colorimetric sensor to the simulated exhaled breath stream, for the purposes of calibration, or exhaled breath, in actual use, the colorimetric sensor would be immediately removed from the apparatus, placed face up under the LED-lit enclosure when controlled lighting is desired, and the color determined such as by photography, such as with a smartphone camera, followed by determination of the color of the colorimetric sample using a quantitative color scale.

Figure 2:
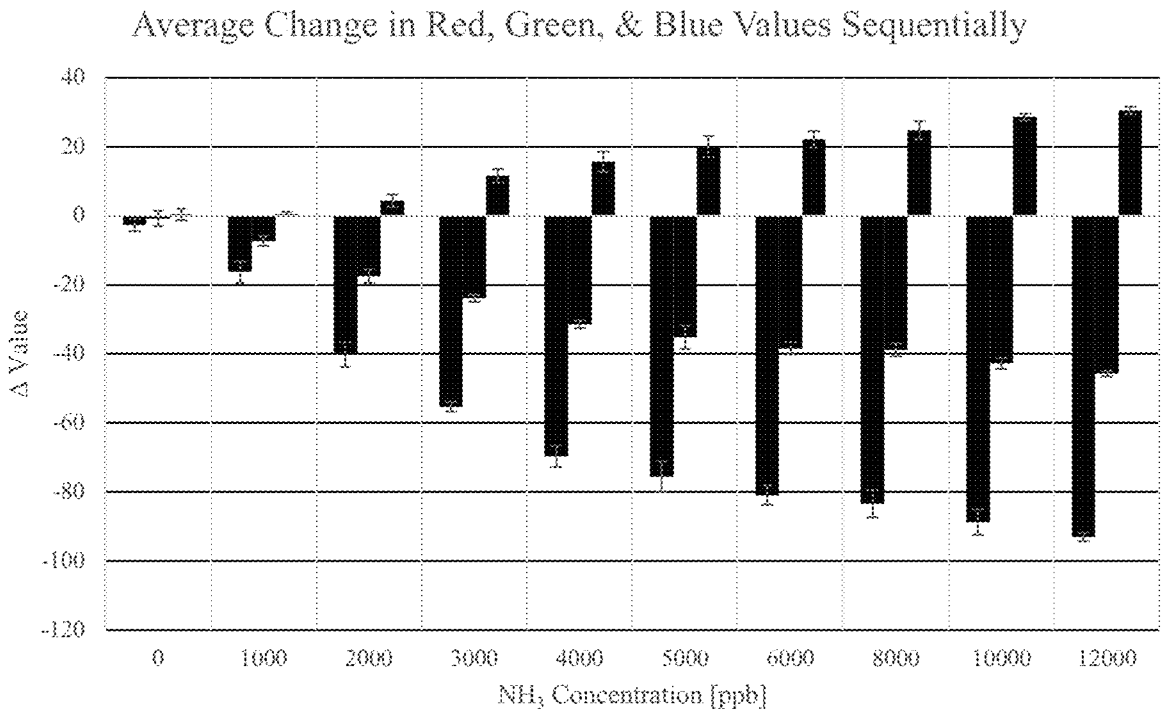
FIG. 2 is a graphical representation of an embodiment of the invention.

For the purposes of demonstration of the invention, the images could be saved and imported into an RGB color-analysis system. It is preferable to average the RGB values for a group of N samples. A representative graph of the average change in Red, Green and Blue is illustrated in FIG. 2 wherein the colors are illustrated sequentially for each sample from left to right with red being on the left and blue being on the right. Statistics for the red color change of the sensors during calibration testing are illustrated graphically in Table 2 wherein the 0-red to 12000-red (ppb $NH_3$) have standard deviations of <5%. The grouping information using the Tukey Method and 95% confidence for the red response of the calibration sensors is provided in Table 3. Statistics for the green color change of the sensors during calibration testing are provided in Table 4 wherein 0-Green to 12000-Green (ppb $NH_3$) have standard deviations <5%. The grouping information using the Tukey Method and 95% confidence for the green response of the calibration sensors is provided in Table 5. Statistics for the blue color change of the sensors during calibration testing are provide in Table 6 wherein 0-Blue to 12000-Blue (ppb $NH_3$) have standard deviations <5%. The grouping information using the Tukey Method and 95% confidence for the blue response of the calibration sensors is provided in Table 7. Statistics for the total color change of the sensors during calibration testing are provided in Table 8 wherein 0-RGB to 12000-RGB (ppb $NH_3$) have standard deviations <5%. Results of analysis of variance using the Tukey Method and 95% confidence for the total color change response of the calibration sensors are provided in Table 9. The grouping information using the Tukey Method and 95% confidence for the total color change response of the calibration sensors are provided in Table 10.

TABLE 2

| $NH_3$ Concentration (ppb) | N | Mean | St. Dev. | 95% CI |
|---|---|---|---|---|
| 0-Red | 10 | −2.645 | 1.749 | (−4.605, −0.685) |
| 1000-Red | 12 | −16.269 | 3.187 | (−18.058, −14.479) |
| 2000-Red | 11 | −40.20 | 3.54 | (−42.07, −38.33) |
| 3000-Red | 12 | −55.245 | 1.430 | (−57.035, −53.456) |
| 4000-Red | 10 | −69.600 | 3.103 | (−71.560, −67.639) |
| 5000-Red | 11 | −75.45 | 4.39 | (−77.32, −73.58) |
| 6000-Red | 10 | −80.824 | 2.796 | (−82.784, −78.863) |
| 8000-Red | 8 | −83.34 | 3.95 | (−85.53, −81.14) |
| 10000-Red | 3 | −88.66 | 3.68 | (−92.24, −85.09) |
| 12000-Red | 3 | −92.939 | 1.213 | (−96.518, −89.360) |

TABLE 3

| $NH_3$ Concentration (ppb) | N | Mean | Grouping | | | | | | | | |
|---|---|---|---|---|---|---|---|---|---|---|---|
| 0-Red | 10 | −2.645 | A | | | | | | | | |
| 1000-Red | 12 | −16.269 | | B | | | | | | | |
| 2000-Red | 11 | −40.20 | | | C | | | | | | |
| 3000-Red | 12 | −55.245 | | | | D | | | | | |
| 4000-Red | 10 | −69.600 | | | | | E | | | | |
| 5000-Red | 11 | −75.45 | | | | | | F | | | |
| 6000-Red | 10 | −80.824 | | | | | | | G | | |
| 8000-Red | 8 | −83.34 | | | | | | | G | H | |
| 10000-Red | 3 | −88.66 | | | | | | | | H | I |
| 12000-Red | 3 | −92.939 | | | | | | | | | I |

Means that do not share a letter are significantly different.

TABLE 4

| $NH_3$ Concentration (ppb) | N | Mean | St. Dev. | 95% CI |
|---|---|---|---|---|
| 0-Green | 10 | −0.723 | 2.212 | (−1.939, 0.493) |
| 1000-Green | 12 | −7.253 | 1.380 | (−8.363, −6.143) |
| 2000-Green | 11 | −17.429 | 1.959 | (−18.588, −16.270) |
| 3000-Green | 12 | −23.858 | 1.035 | (−24.968, −22.748) |
| 4000-Green | 10 | −31.402 | 1.132 | (−32.618, −30.186) |
| 5000-Green | 11 | −35.15 | 3.36 | (−36.31, −33.99) |
| 6000-Green | 10 | −38.352 | 1.729 | (−39.568, −37.137) |
| 8000-Green | 8 | −38.746 | 1.926 | (−40.105, −37.387) |
| 10000-Green | 3 | −42.764 | 1.582 | (−44.984, −40.545) |
| 12000-Green | 3 | −45.683 | 0.780 | (−47.902, −43.463) |

TABLE 5

| $NH_3$ Concentration (ppb) | N | Mean | Grouping | | | | | | | |
|---|---|---|---|---|---|---|---|---|---|---|
| 0-Green | 10 | −0.723 | A | | | | | | | |
| 1000-Green | 12 | −7.253 | | B | | | | | | |
| 2000-Green | 11 | −17.429 | | | C | | | | | |
| 3000-Green | 12 | −23.858 | | | | D | | | | |
| 4000-Green | 10 | −31.402 | | | | | E | | | |
| 5000-Green | 11 | −35.15 | | | | | | F | | |
| 6000-Green | 10 | −38.352 | | | | | | | G | |
| 8000-Green | 8 | −38.746 | | | | | | | G | H |

TABLE 5-continued

| $NH_3$ Concentration (ppb) | N | Mean | Grouping |
|---|---|---|---|
| 10000-Green | 3 | −42.764 | H I |
| 12000-Green | 3 | −45.683 | I |

Means that do not share a letter are significantly different.

TABLE 6

| $NH_3$ Concentration (ppb) | N | Mean | St. Dev. | 95% CI |
|---|---|---|---|---|
| 0-Blue | 10 | 0.414 | 1.665 | (−0.955, 1.784) |
| 1000-Blue | 12 | 0.582 | 0.573 | (−0.668, 1.832) |
| 2000-Blue | 11 | 4.389 | 1.821 | (3.083, 5.695) |
| 3000-Blue | 12 | 11.603 | 1.959 | (10.353, 12.853) |
| 4000-Blue | 10 | 15.677 | 2.924 | (14.307, 17.047) |
| 5000-Blue | 11 | 20.061 | 3.030 | (18.755, 21.367) |
| 6000-Blue | 10 | 22.126 | 2.417 | (20.757, 23.496) |
| 8000-Blue | 8 | 24.782 | 2.661 | (23.251, 26.314) |
| 10000-Blue | 3 | 28.685 | 0.968 | (26.184, 31.186) |
| 12000-Blue | 3 | 30.555 | 1.061 | (28.054, 33.055) |

TABLE 7

| $NH_3$ Concentration (ppb) | N | Mean | Grouping |
|---|---|---|---|
| 12000-Blue | 3 | 30.555 | A |
| 10000-Blue | 3 | 28.685 | A B |
| 8000-Blue | 8 | 24.782 | B C |
| 6000-Blue | 10 | 22.126 | C D |
| 5000-Blue | 11 | 20.061 | D |
| 4000-Blue | 10 | 15.677 | E |
| 3000-Blue | 12 | 11.603 | F |
| 2000-Blue | 11 | 4.389 | G |
| 1000-Blue | 12 | 0.582 | H |
| 0-Blue | 10 | 0.414 | H |

Means that do not share a letter are significantly different.

TABLE 8

| $NH_3$ Concentration (ppb) | N | Mean | St. Dev. | 95% CI |
|---|---|---|---|---|
| 0-RGB | 10 | 4.009 | 1.188 | (1.877, 6.141) |
| 1000-RGB | 12 | 17.835 | 3.444 | (15.889, 19.781) |
| 2000-RGB | 11 | 44.08 | 3.99 | (42.04, 46.11) |
| 3000-RGB | 12 | 61.319 | 1.539 | (59.373, 63.265) |
| 4000-RGB | 10 | 78.004 | 3.119 | (75.873, 80.136) |
| 5000-RGB | 11 | 85.69 | 5.15 | (83.66, 87.72) |
| 6000-RGB | 10 | 92.197 | 2.921 | (90.065, 94.329) |
| 8000-RGB | 8 | 95.22 | 4.25 | (92.84, 97.61) |
| 10000-RGB | 3 | 102.54 | 3.92 | (98.65, 106.43) |
| 12000-RGB | 3 | 107.979 | 1.046 | (104.087, 111.871) |

TABLE 9

| Source | DF | Seq SS | Contribution | Adj SS | Adj MS | F-Value | P-Value |
|---|---|---|---|---|---|---|---|
| Factor | 9 | 98480.5 | 99.08% | 98480.5 | 10942.3 | 953.65 | 0.000 |
| Error | 80 | 917.9 | 0.92% | 917.9 | 11.5 | | |
| Total | 89 | 99398.4 | 100.00% | | | | |

TABLE 10

| $NH_3$ Concentration (ppb) | N | Mean | Grouping |
|---|---|---|---|
| 12000-RGB | 3 | 107.979 | A |
| 10000-RGB | 3 | 102.54 | A B |
| 8000-RGB | 8 | 95.22 | B C |
| 6000-RGB | 10 | 92.197 | C |
| 5000-RGB | 11 | 85.69 | D |
| 4000-RGB | 10 | 78.004 | E |
| 3000-RGB | 12 | 61.319 | F |
| 2000-RGB | 11 | 44.08 | G |
| 1000-RGB | 12 | 17.835 | H |
| 0-RGB | 10 | 4.009 | I |

Means that do not share a letter are significantly different.

Figure 3:
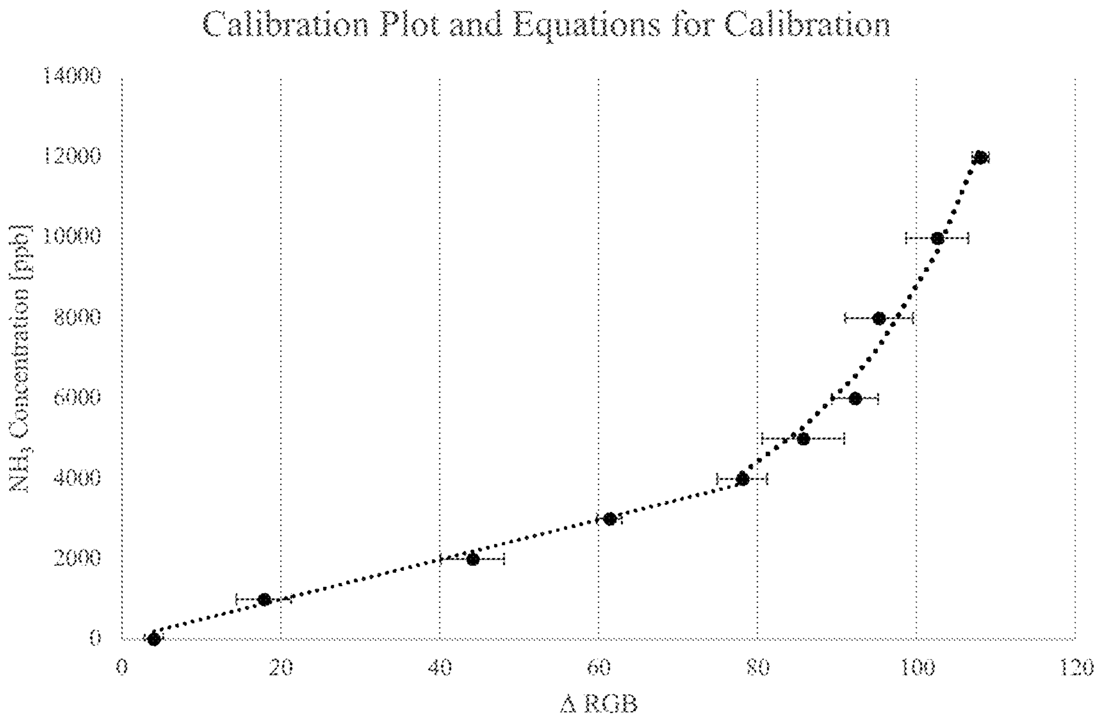
FIG. 3 is a graphical representation of an embodiment of the invention.

A Plot and accompanying lines of best fit of the total color change response of the calibration sensors is illustrated graphically in FIG. 3 wherein the lower region is up to 80 ΔRGB and the higher region is above 80 ΔRGB, with ΔRGB representing the difference in the RGB color change compared to the non-contacted portion of the sensor discs that was protected from the gas stream by the white plastic donut using the formula of $\Delta RGB = \text{Square Root } [(\Delta R)^2+(\Delta G)^2+(\Delta B)^2]$. The inflection point of the data is at 4,000 ppb; a linear equation characterizes the lower region and a rational equation characterizes the higher region.

The calibration results were based on 90 colorimetric disc sensors. Repeat samples were completed at increasing levels of gaseous ammonia to create a plot of total color change versus ammonia concentration. One-L gas samples provided adequate sensitivity and 1 L of exhaled breath was an appropriate amount to ask of a patient based on preliminary studies. Typical users took approximately 15-20 seconds to exhale 1-L of exhaled breath through the apparatus. This noted time for testing is the basis for the use of 4 LPM as the calibration flowrate. Furthermore, a user can easily maintain a pressure reading of 4-5 water column inches (in. wc) on the pressure gauge during use, and a 4 LPM flowrate corresponded to a 4 in. wc pressure on the pressure gauge. These constants were selected to replicate end-user considerations. Due to observations seen in the preliminary work, two gas cylinders were used for calibrations (one cylinder of 5% $CO_2$-in-air, and the other with either 20 ppm or 30 ppm $NH_3$-in-air). Sensors were exposed to 1-L of gas sample and immediately imaged. The images were processed and analyzed using a MATLAB code.

For the purposes of demonstration of the invention a representative MATLAB code is:

```
clear
clc
close all
% create blank arrays to store sample values
differenceinR_array=[ ];
differenceinG_array=[ ];
differenceinB_array=[ ];
colorchangeinRGB_array=[ ];
for i=1:3%
read images based on their stored file name; the number
    after Patient, this will change for each patient tested
filename=strcat('Patient-6-',num2str(i),'.png');
sample=imread(filename);
sample_lab=rgb2lab(sample);
ab=sample_lab(:,:,2:3);
ab=im2single(ab);
% use k-means to recognize two color clusters in the
    image
```

```
[L, centers]=imsegkmeans(ab,2,'NumAttempts',3);
% get the size of the 2D array to iterate through the R,G,B layers
dim=size(sample);
len=dim(1)*dim(2);
% choose which labels from k-means to get indices of; label 1 is the cluster with more pixels
morepixel=find(L==1);
lesspixel=find(L==2);
% compute averages for the RGB values of the two clusters
r1=sum(sample(morepixel))/length(morepixel);
g1=sum(sample(morepixel+len))/length(morepixel);
b1=sum(sample(morepixel+(2*len)))/length(morepixel);
r2=sum(sample(lesspixel))/length(lesspixel);
g2=sum(sample(lesspixel+len))/length(lesspixel);
b2=sum(sample(lesspixel+(2*len)))/length(lesspixel);
if r2>r1
% a larger r2 value indicates r2, b2, g2 are the yellow part of the sensor
mask1=L==2;
% sample_lab(:,:,x) is just one of the L, a, or b values
% this applies the mask over the image, only showing the parts in the mask
cluster1=double(sample_lab(:,:,1)).*double(sample_lab(:,:,3)).*mask1;
% computes the difference in values by subtracting yellow part of sensor from blue part of sensor
differenceinR=(r1-r2);
differenceinG=(g1-g2);
differenceinB=(b1-b2);
% outputs the RGB values and change in color for the sensor
fprintf('Sample: %.1f\n',i)
fprintf('Average RGB Values for Yellow Area of Sensor R: %.2f G: %.2f B: %.2f\n',r2,g2,b2)
fprintf('Average RGB Values for Blue Area of Sensor R: %.2f G: %.2f B: %.2f\n',r1,g1,b1)
fprintf('Change in Values R: %.2f G: %.2f B: %.2f\n', differenceinR,differenceinG,differenceinB)
else
mask1=L==1;
cluster1=double(sample_lab(:,:,1)).*double(sample_lab(:,:,3)).*mask1;
% computes the difference in values by subtracting yellow part of sensor from blue part of sensor
differenceinR=(r2-r1);
differenceinG=(g2-g1);
differenceinB=(b2-b1);
% outputs the RGB values and change in color for the sensor
fprintf('Sample: %.1f\n',i)
fprintf('Average RGB Values for Yellow Area of Sensor R: %.2f G: %.2f B: %.2f\n',r1,g1,b1)
fprintf('Average RGB Values for Blue Area of Sensor R: %.2f G: %.2f B: %.2f\n',r2,g2,b2)
fprintf('Change in Values R: %.2f G: %.2f B: %.2f\n', differenceinR,differenceinG,differenceinB)
end
% create figures to show the original images
FIG. (1)
subplot(3, 5, i)
imshow(sample)
title(filename)
% create figures to show the clustered images
figure(2)
subplot(3, 5, i)
imshow(cluster1)
title(filename)
% computes total change in color
totalcolorchange=sqrt((differenceinR)A2+(differenceinG)A2+(differenceinB)A2);
% outputs color change to the command window
fprintf('Total Color Change: %.2f\n\n',totalcolorchange)
% stores the changes in R, G, & B values into their respective vectors
differenceinR_array(i)=differenceinR;
differenceinG_array(i)=differenceinG;
differenceinB_array(i)=differenceinB;
colorchangeinRGB_array(i)=totalcolorchange;
end
% computes the means of each vector
differenceinR_avg=mean(differenceinR_array);
differenceinG_avg=mean(differenceinG_array);
differenceinB_avg=mean(differenceinB_array);
colorchangeinRGB_avg=mean(colorchangeinRGB_array);
% computes the standard deviation of each vector
differenceinR_std=std(differenceinR_array);
differenceinG_std=std(differenceinG_array);
differenceinB_std=std(differenceinB_array);
colorchangeinRGB_std=std(colorchangeinRGB_array);
% exports data to excel
writematrix(differenceinR_array,'export data.xlsx', 'Sheet',1,'Range','A1')
writematrix(differenceinG_array,'export data.xlsx', 'Sheet',1,'Range','A2')
writematrix(differenceinB_array,'export data.xlsx', 'Sheet',1,'Range','A3')
writematrix(colorchangeinRGB_array,'export data.xlsx', 'Sheet',1,'Range','A4')
% output values to command window
fprintf('Change in R Value: Average %.2f Std. Dev: %.2f\n',differenceinR_avg,differenceinR_std)
fprintf('Change in G Value: Average %.2f Std. Dev: %.2f\n',differenceinG_avg,differenceinG_std)
fprintf('Change in B Value: Average %.2f Std. Dev: %.2f\n',differenceinB_avg,differenceinB_std)
fprintf('Total Color Change: Average %.2f Std. Dev:
%.2f\n\n',colorchangeinRGB_avg,colorchangeinRGB_std).
```

As the concentration of $NH_3$ increases, the colorimetric disc sensor becomes increasingly more green. The sensor's original color is yellow and has average RGB values of 155, 120, and 15, respectively. Exposure to basic, gaseous ammonia changes the sensor's color to green. These value changes are detected by a MATLAB code that clusters the image into two groups with the inherent assumption that there will be two groups within the image. This explains why MATLAB outputs a slight color change for the 0 ppm samples even though there is no discernable color change of the 0 ppm sensor. It is further recognized that there is no color change of the sensor as the MATLAB code does not detect the circular area in the 0 ppm sample that was exposed to the analyte. The 1 ppm and 2 ppm samples clearly indicate a color change.

MATLAB calculates the change in RGB values between the two segments of the sensor by taking the RGB values of the green region and subtracting the RGB values of the yellow region. The averages and standard deviations of these changes are shown in FIG. 2. As $NH_3$ concentration increases, the changes in the RGB values change increasingly. The most sensitive region of change is in the lower $NH_3$ concentrations for these samples and the changes begin to saturate at the higher concentrations.

The change in red values had the lowest standard deviations and therefore the change in red value is preferably used for the calibration plots. However, as seen in Table 3, after the concentration of ammonia reaches greater than about 4,000 ppb (4 ppm), the groups of 6,000-8,000, 8,000-10000, and 10000-12000 are not significantly different, while the color change between these three groupings is statistically significant. A similar trend was identified for the green and blue values. The blue values also showed similarity at lower levels of ammonia.

The use of the white donut cover over the sensor protects the outer yellow region of the sensor with the central region of the sensor exposed to the gas stream.

The sensor's change in color is due to the basic ammonia reacting with the bromocresol green indicator embedded in the substrate. This is a surface reaction which is limited by the available BCG reactant on the exposed area of the sensor. Therefore, the technology will reach a saturation limit.

To enhance sensitivity of the design, the MATLAB code computes and sums the changes in red, green, and blue values to obtain the total color change by the following equation:

$$\Delta RGB = \sqrt{(\Delta R)^2 + (\Delta G)^2 + (\Delta B)^2}$$

Averages and standard deviations of the total color change were received from the MATLAB code. Tables 8 through 10 provide the statistics and ANOVA one-way comparisons of the total color change by $NH_3$ concentration. As seen in Tables 9 and 10 statistically significant differences ($p<0.001$) were detected at 1,000 ppb intervals of humidified, gaseous ammonia at clinically relevant concentrations (between 0 and 6,000 ppb). Table 10 provides the grouping information, where the saturation effect is seen to begin after 4,000 ppb $NH_3$ concentration. While there is still a clear increase in value, the samples of groupings of 6000-8000, 8000-10000, and 10000-12000 are not significantly different, while the color change between these three groupings is statistically significant.

Total color change (on the x-axis) is plotted against $NH_3$ concentration [ppb] (on the y-axis) in the final calibration plot, provided in FIG. 3 where a linear equation characterizes the lower region and a rational function characterizes the higher region. The linear equation is $NH_3=49.66*\Delta RGB$ ($R^2=0.9965$) and the rational function is $$NH_3 = \frac{2990.78 * \Delta RGB}{134.33 - \Delta RGB}(R^2 = 0.9775).$$

These two lines of best fit and the inflection point of 4,000 ppb were chosen for multiple reasons. First, it is clear from the graph that there is a linear to nonlinear shift that occurs around the 4,000 ppb data point. Additionally, 4,000 ppb was selected based on findings in the literature and minimization of residual error. Based on published literature on ammonia levels in the exhaled breath, the critical range of ammonia concentrations was taken to be from 0-4,000 ppb and more preferably 0-12,000 ppb.

The y-intercept of the line of best fit was adjusted to be zero as a 0 ppb sample should theoretically provide zero change in color. Visually, there is no color change in the 0 ppb sensor samples. However, due to the inherent assumption embedded in the MATLAB code that detects two groups in the imported images, the program will find two groupings in any image and compute the difference between them. When extracting data from the 0 ppb images, it segments two groups that are extremely similar in RGB values which is why the total color change is so minimal. To accommodate for this issue, the y-intercept of the linear calibration equation is adjusted to zero. This linear equation also provided a correlation value of 0.997.

A rational function was used to characterize the higher region of the data since the data appears to be reaching a vertical asymptote around 115. After about 4,000 ppb, even as concentrations of gaseous ammonia increased, the color change was trending toward that vertical asymptote, or saturation limit. This phenomenon is due to the nature of the technology; the reaction between BCG and gaseous ammonia is a surface reaction which depends on the amount of BCG reactant available. Therefore, as the amount of unreacted BCG available decreases to zero, the total change in color will reach a maximum saturation limit. The rational function was determined in Excel using data solver to minimize the sum of residual squares. Further, this equation provided a correlation value of 0.9775.

The least squares method was used to confirm 4,000 ppb was an appropriate inflection point with the aforementioned lines of best fit. 3,000, 4,000, and 5,000 ppb were investigated as points of inflection, and 4,000 ppb was confirmed as the appropriate choice as it minimized the sum of the residuals.

The calibration plot is provided in FIG. 3 quantitatively characterize the apparatus. These equations were used for calculating the ammonia concentration of exhaled breath for the patients who partook in the clinical trials. A sensor response with a total change in color equal to or less than 78 will calculate ammonia concentrations via the linear function, while a color change greater than 78 will calculate ammonia concentrations via the rational function.

Clinical Examples

The apparatus was evaluated for patients with chronic kidney disease (CKD) at stages 1, 3, and 5, with patients at stage 1 disease representing the control group that should have minimal elevation of breath ammonia concentration. The components of the apparatus were sterilized by autoclaving before use, and individual, disposable mouthpieces and sample bags were used for each test. The device was assembled in-clinic.

After assembly, patients were handed the device and asked to place the mouthpiece in their mouth, inhale through their nose and exhale through the mouthpiece into the device while maintaining between 4 and 5 inches of water column (wc) static pressure reading on the pressure gauge. This breathing technique was continued until the 1-L Tedlar gas-sampling bag at the outlet arm of the device was full, thus providing control of sample volume (1-L total volume). The sample bag was sealed and removed, and the bottom cap containing the colorimetric disc sensor was removed. The sensor was removed, placed under the LED-lit enclosure to control for ambient lighting, and the resulting color change was photographed using a smartphone camera. The image was analyzed using the MATLAB program to extract the total color change of the sensor. The total color change was used to calculate the breath ammonia levels in the exhaled breath via the calibration curves as previously described. These results were documented in the secure database after de-identification.

Patients completed this study during their routine clinic visit, so blood tests were also performed around the time of testing. The metrics determined from the blood sample which included blood urea nitrogen (BUN), creatinine levels, and estimated glomerular filtration rate (eGFR) were also entered into the secure database after de-identification. These metrics were compared to the results obtained from the exhaled breath test to evaluate the level of correlation.

For the clinical evaluation, a set of at least three patients each with stage 1, 3, and 5 CKD were tested. Three independent tests for each patient provided statistical data on the performance of the exhaled breath ammonia sensors. The breath ammonia concentrations were averaged together for each patient to calculate their mean value, thus providing a group sampling of at least N=3 for each CKD stage. The values were statistically analyzed by one-way analysis of variance (ANOVA) with post-hoc Tukey multiple comparison to determine if the measured breath ammonia levels were significantly different ($p<0.05$) between the stage 1, 3, and 5 patients. Values for each group were plotted versus BUN, blood creatinine values, and eGFR, which are normally determined at each clinical visit, to assess the level of correlation between these metrics. Significantly elevated breath ammonia levels between CKD patient populations were predicted, and it was anticipated that there will be a correlation between exhaled breath ammonia and BUN, eGFR, and creatinine levels. The compiled patient data from pilot clinical trials is provided in Table 11. The blood urea nitrogen (BUN) levels plotted against detected breath ammonia ($NH_3$) levels, N=3, per patient are provided in FIG. 4. The blood creatinine values plotted versus blood urea nitrogen (BUN) levels and breath ammonia ($NH_3$) levels, N=3, per patient is provided in FIG. 5. The calculated eGFR plotted versus blood urea nitrogen (BUN) levels and breath ammonia ($NH_3$) levels, N=3, per patient is provided in FIG. 6. The blood urea nitrogen (BUN) levels and breath ammonia ($NH_3$) levels, N=3, per patient characterized by stage of chronic kidney disease (CKD) is provided in FIG. 7. The statistics on detected levels of breath ammonia in exhaled breath by stage of chronic kidney disease is provided in Table 12. The results of analysis of variance with 95% confidence for comparing the levels of breath ammonia by stage of chronic kidney disease are provided in Table 13. The results of Tukey Simultaneous Tests for differences of means with 95% confidence for the levels of breath ammonia by stage of chronic kidney disease are provided in Table 14.

TABLE 11

| Patient # | Avg. $NH_3$ Conc. [ppb] | Std. Dev. | BUN Level [mg/dL] | Creatinine [mg/dL] | eGFR | Stage |
|---|---|---|---|---|---|---|
| 1 | 1370 | 51.5 | 12 | 0.6 | >90 | 1 |
| 5 | 3530 | 281 | 18 | 0.47 | >90 | 1 |
| 8 | 173 | 71.3 | 12 | 0.98 | >90 | 1 |
| 10 | 1320 | 163 | 16 | 0.58 | >90 | 1 |
| 2 | 1500 | 56.8 | 21 | 0.95 | 57 | 3 |
| 6 | 3530 | 312 | 35 | 1.37 | 50 | 3 |
| 7 | 1560 | 113 | 22 | 3.11 | 30 | 3 |
| 3 | 5420 | 1350 | 58 | 5.5 | 10 | 5 |
| 3* | 323 | 125 | 11 | N/A | N/A | 5 |
| 4 | 8220 | 1110 | 50 | 2.86 | 10 | 5 |
| 9 | 5920 | 925 | 58 | 9.96 | 10 | 5 |

3* sample indicates Patient #3 exhaled breath and BUN results post-dialysis.

TABLE 12

| Factor | N | Mean $NH_3$ Conc, [ppb] | St. Dev. | 95% CI |
|---|---|---|---|---|
| Stage 1 | 12 | 1598 | 1275 | (814, 2382) |
| Stage 3 | 9 | 2199 | 1016 | (1293, 3105) |
| Stage 5 | 9 | 6520 | 1628 | (5615, 7426) |

TABLE 13

| Source | DF | Seq SS | Contribution | Adj SS | Adj MS | F-Value | P-Value |
|---|---|---|---|---|---|---|---|
| Factor | 2 | 138953543 | 74.59% | 138953543 | 69476771 | 39.62 | 0.000 |
| Error | 27 | 47345008 | 25.41% | 47345008 | 1753519 | | |
| Total | 29 | 186298551 | 100.00% | | | | |

TABLE 14

| Difference of Levels | Difference of Means | SE of Difference | 95% CI | T-Value | Adjusted P-Value |
|---|---|---|---|---|---|
| Stage 3-Stage 1 | 601 | 584 | (−848, 2050) | 1.03 | 0.565 |
| Stage 5-Stage 1 | 4922 | 584 | (3473, 6372) | 8.43 | 0.000 |
| Stage 5-Stage 3 | 4322 | 624 | (2772, 5871) | 6.92 | 0.000 |

Individual confidence level = 98.04%

The clinical trial was completed with pediatric patients suffering from stage 1, 3, and 5 chronic kidney disease. Patients were anywhere from 8 to 18 years of age, and clinic appointments were completed at all times of the day. Further, since patients were recruited during their visit and not before, they were not required to adhere to any dietary, fasting, or oral hygiene conditions prior to testing.

The results demonstrate the potential for providing evidence for the deployment of the developed technology as a simple, low-cost way for patients to personally monitor their disease progression from the comfort of their home. Images of the colorimetric sensors after three independent exhaled breath tests were completed by a patient at stage 1, 3 and 5 CKD respectively. There was a distinct increase in color change observed between the stages. The repeatability of the system was also observed. While the standard deviations for the three tests is minimal for those of lower CKD stages, this variation is increased for stage 5 patients.

Table 11 provides the compiled patient data from the ten patients who participated in the pilot clinical trial. The average detected breath ammonia level, N=3, and standard deviations are provided for each patient as well as their corresponding blood urea nitrogen (BUN) level, creatinine level, estimated glomerular filtration rate (eGFR), and stage of disease.

Figure 4:
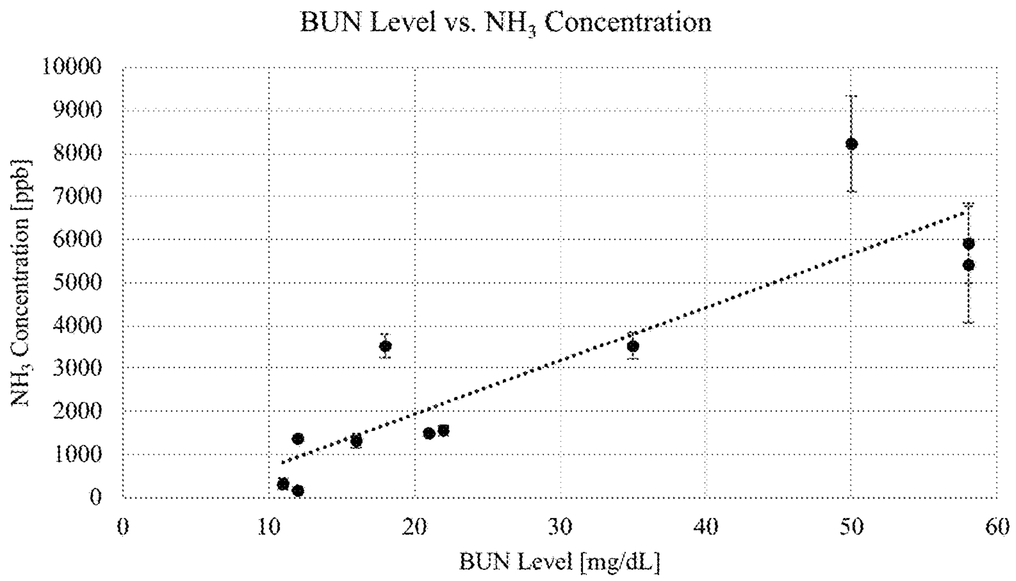
FIG. 4 is a graphical representation of an embodiment of the invention.
Figure 5:
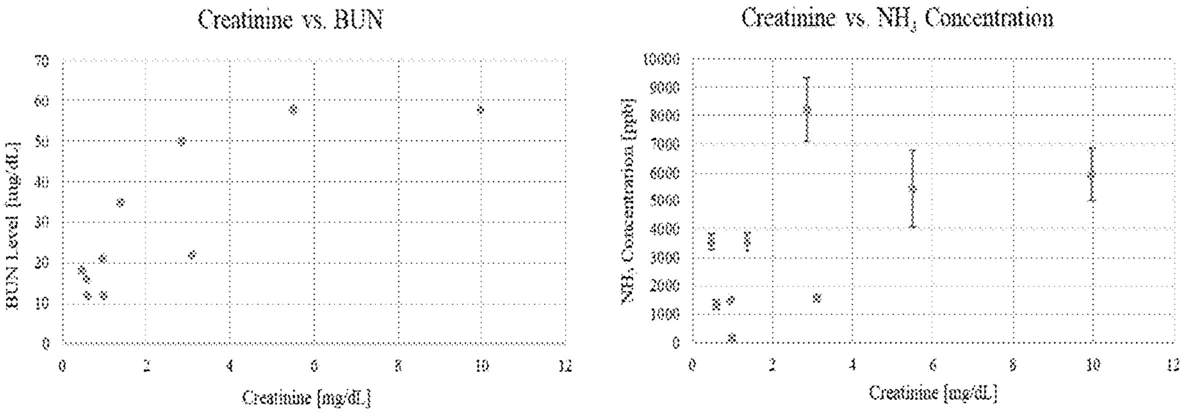
FIG. 5 is a graphical representation of an embodiment of the invention.
Figure 6:
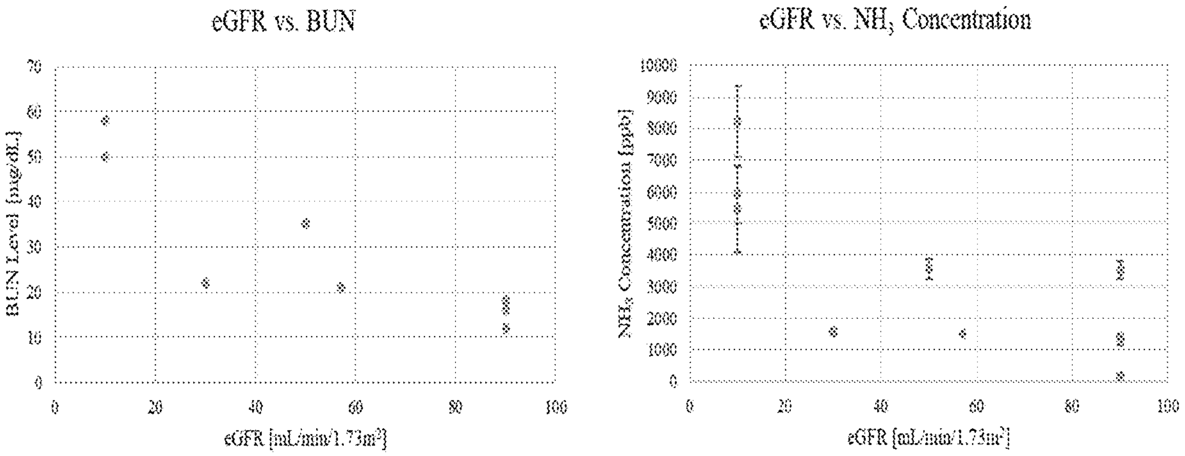
FIG. 6 is a graphical representation of an embodiment of the invention.
Figure 7:
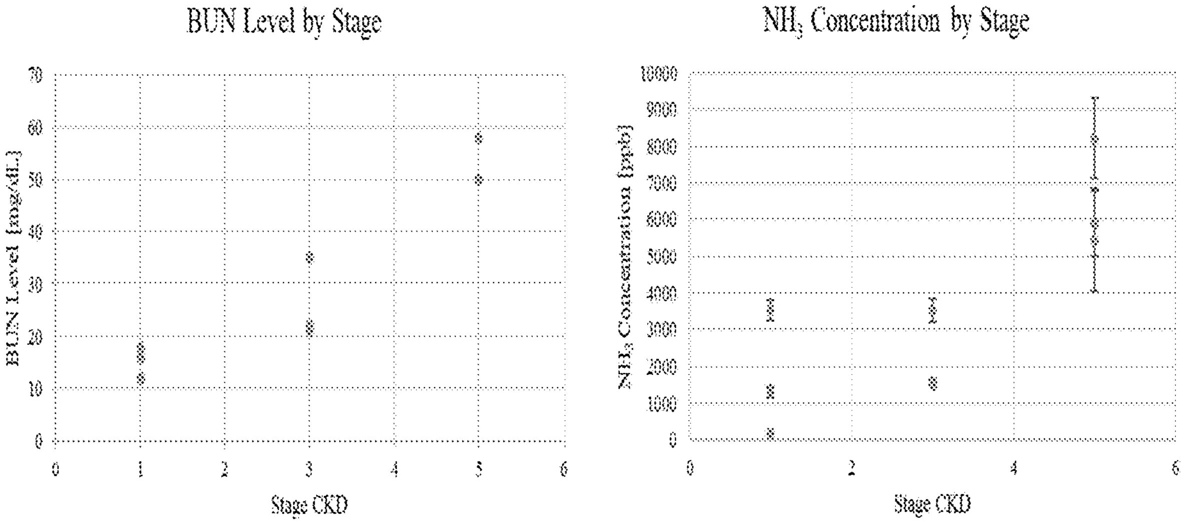
FIG. 7 is a graphical representation of an embodiment of the invention.

FIG. 4 graphically illustrates the patient BUN levels plotted against the detected level of breath ammonia. There was a strong linear correlation with a best-fit equation of $y=124.15x-544.37$ ($R^2=0.794$) between blood urea nitrogen (BUN) levels and breath ammonia ($NH_3$) levels providing evidence that breath ammonia levels can be used as a non-invasive way of predicting BUN levels. FIG. 5-7 show BUN levels and exhaled $NH_3$ levels plotted versus creatinine levels, eGFR, and CKD stage. There was not a strong linear correlation found between breath ammonia levels and any other metric. No or weak correlation was found between breath ammonia levels and eGFR and serum creatinine for pediatric CKD patients and healthy controls. Nonetheless, the data from this study correlating BUN levels with creatinine levels, eGFR, and stage are similar in trend to the data correlating breath $NH_3$ concentrations with the same metrics.

Table 12 provides the statistics on detected levels of $NH_3$ in exhaled breath by stage of chronic kidney disease. Table 13 shows the results of ANOVA with 95% confidence comparing the levels of breath ammonia by stage of disease ($F=39.62$ and $p<0.001$). Further, Table 14 shows the results of Tukey simultaneous tests for differences of means with 95% confidence for the levels of breath ammonia by stage of disease. Stage 5 patients were statistically significantly different than stage 1 and 3 respectively ($p<0.001$), but there was not a statistically significant difference ($p=0.565$) between stage 1 and 3. However, applying the Tukey Method to the corresponding BUN levels of patients grouped by stage of disease did not give a statistically significant difference ($p=0.055$) between stage 1 and 3 either. Therefore, it can be concluded that the prototype successfully detected levels of breath ammonia in the exhaled breath, or breath ammonia, of patients staged 1, 3, and 5, and the detected $NH_3$ concentrations strongly correlated with BUN levels.

Variability in results seen from patients of the same stage may be explained by differences in diet, dental hygiene, and breathing pattern.

Some studies have shown that different phases of a single exhale may have different levels of trace compounds in them. Breath exhalation may be broken into three phases. Phase I, or the start of exhalation, is mostly anatomical dead space, i.e. consisting of the air that was just inhaled but not mixed with alveolar air. Phase II is where exhaled breath has mixed with alveolar air; this phase is characterized by a large increase in carbon dioxide. Phase III of exhalation is where carbon dioxide levels have plateaued at their peak value. This breath phase contains the most water vapor, comes from the deepest reserves of one's lungs, and thus is the most indicative of the concentrations of analytes present in the blood stream. Therefore, it may be assumed that Phase III exhaled breath will contain a larger amount of breath ammonia since it is more representative of gas concentrations at the alveolar interface which come from the blood stream.

During clinical trials, patients were asked to inhale through their nose and exhale through their mouth into the device while maintaining a constant 4-5 in. wc pressure on the pressure gauge. However, it was observed that some patients completed the test with an increased amount of shallower breaths and others completed the test with only one or two large exhales. Nevertheless, both still maintained the constant 4-5 in. wc pressure during exhalation. Patient 5, stage 1 with BUN level 18 mg/dL, completed the tests with two large exhales and provided a breath ammonia concentration of 3,530 ppb. While Patient 8, stage 1 with BUN level 12 mg/dL, completed the test via a more tidal and shallower breathing pattern and provided a breath ammonia concentration of 173 ppb. If it is assumed that the shallow, tidal breathing pattern contains more Phase I breath while large exhalations contain more Phase III breath, then this difference in breathing pattern could account for the difference in breath ammonia levels observed. This is especially true if Phase III exhalation does contain more water vapor, which has been shown to improve the sensitivity of colorimetric technologies for this particular device.

In one embodiment, it is preferable that the first portion of the exhaled breath be excluded from the data such as the first 200 mL of exhaled breath to minimize the influence of oral cavity contamination or dilution of samples.

The results obtained from the pilot clinical trials provide sufficient evidence to support the deployment of this technology as an easy-to-use, quick, at-home, and low-cost way for a patient to assess and manage their kidney health. While there may be variability between users, there was a decreased deviation observed in the independent tests performed by each patient. Further, the results obtained from Patient 3 before and after hemodialysis eliminated the user-to-user variability and controlled the other considerations such as diet and dental habits, as this patient did not partake in any activities other than hemodialysis in between the testing sessions. The response in sensor trended nicely with the corresponding BUN levels showing that the sensor was selectively responding to ammonia in the exhaled breath.

Statistically significant differences were found between stages 1 and 5 and stages 3 and 5, but not for stages 1 and 3 CKD. However, a strong correlation was found between blood urea nitrogen levels and breath ammonia levels providing evidence that this prototype system could be used as a non-invasive way of tracking BUN levels, thus providing the potential to greatly improve the current cycle of care for the CKD patient population.

Additional Examples

Figure 8:
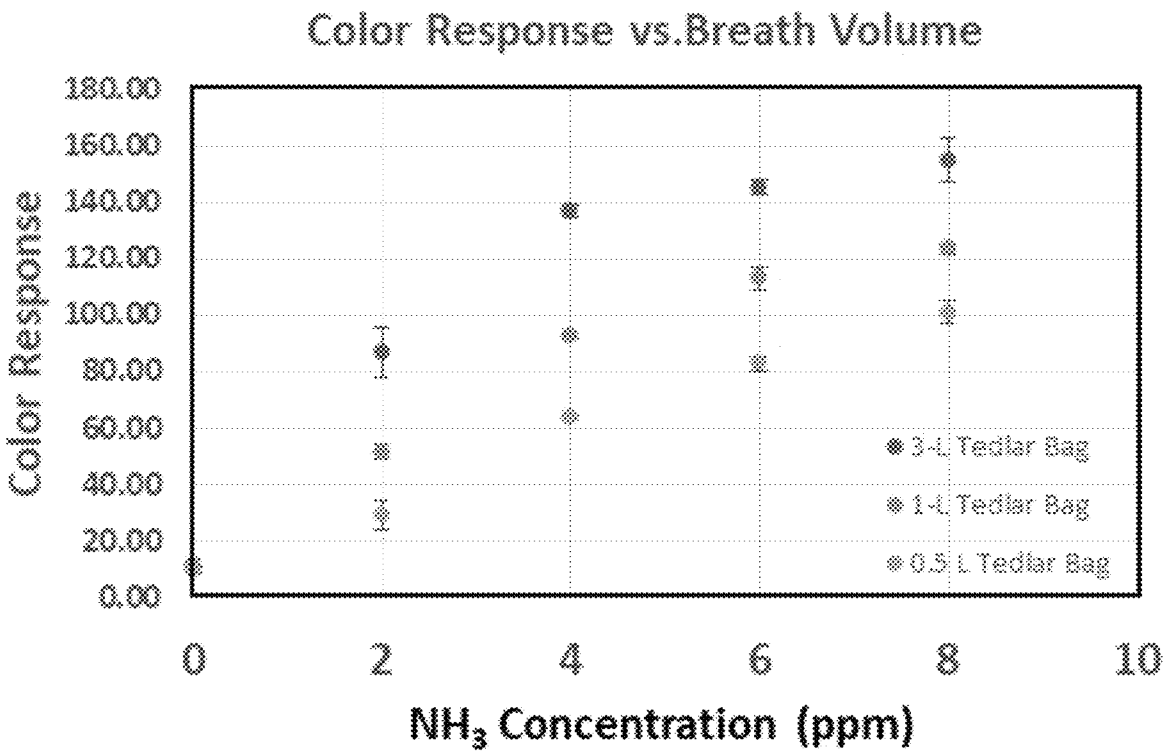
FIG. 8 is a graphical representation of an embodiment of the invention.

The color response of the simulated exhaled breath was evaluated using three sizes of the calibrated Tedlar bags (0.5, 1.0, and 3.0 L volume) to control the total volume of exhaled breath passed through the system during a test when using a 4.0 LPM total gas flow rate. When the concentration of $NH_3$ in the simulated exhaled breath was varied over the physiological range of 0 to 8 ppm, the response of the color-indicating disc increased as the volume of exhaled breath was increased per test. The volume of the exhaled-breath collection bag is thus shown to directly increase the color response, and thus the sensitivity of the breath test for $NH_3$. The results are presented in FIG. 8.

Figure 9:
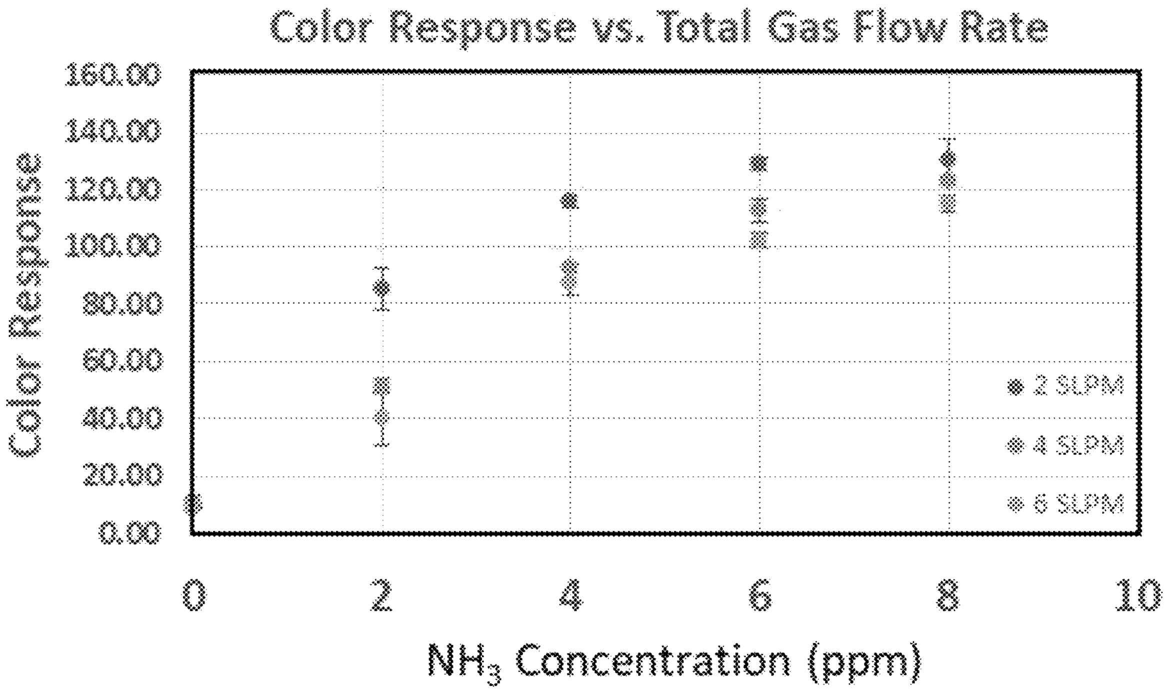
FIG. 9 is a graphical representation of an embodiment of the invention.

The color response of the simulated exhaled breath was evaluated using three different flow rates of simulated exhaled breath (2, 4, and 6 LPM), each using the 1-L Tedlar bag for breath-volume control. The response of the color-indicating disc slightly increases as the flow rate of simulated exhaled breath is decreased. Comparison with the prior slide shows that the color response is not as sensitive to gas flow rate as it is the volume of exhaled breath. The results are presented in FIG. 9

Figure 10:
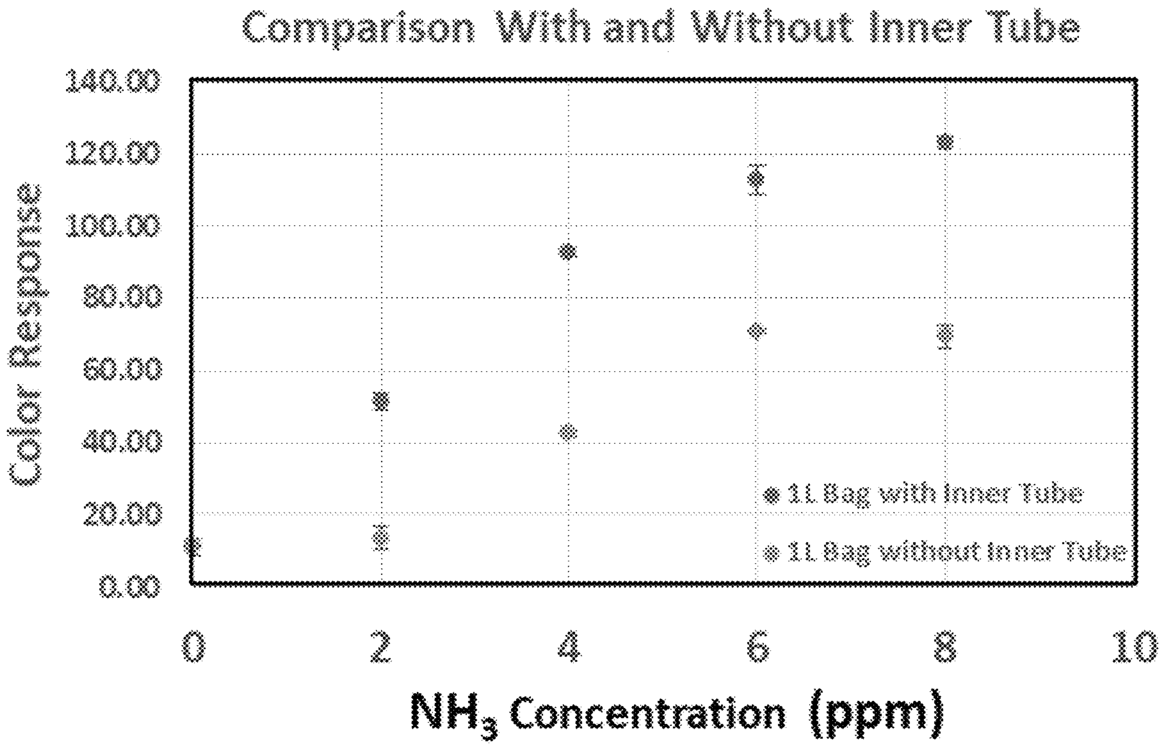
FIG. 10 is a graphical representation of an embodiment of the invention.

Simulated exhaled-breath system with the 1-L Tedlar bag to control breath volume and a 4.0 SLPM total gas flow rate, the color response of the simulated exhaled breath was evaluated with and without the small-diameter internal cylinder in place. With the small-diameter internal cylinder in place to focus the stream of simulated exhaled breath on the center of the color indicating disc, the color response is about 100% greater than the color response that is obtained without the small-diameter internal cylinder in place, thus providing greatly enhanced sensitivity. The results are provided in FIG. 10

Figure 11:
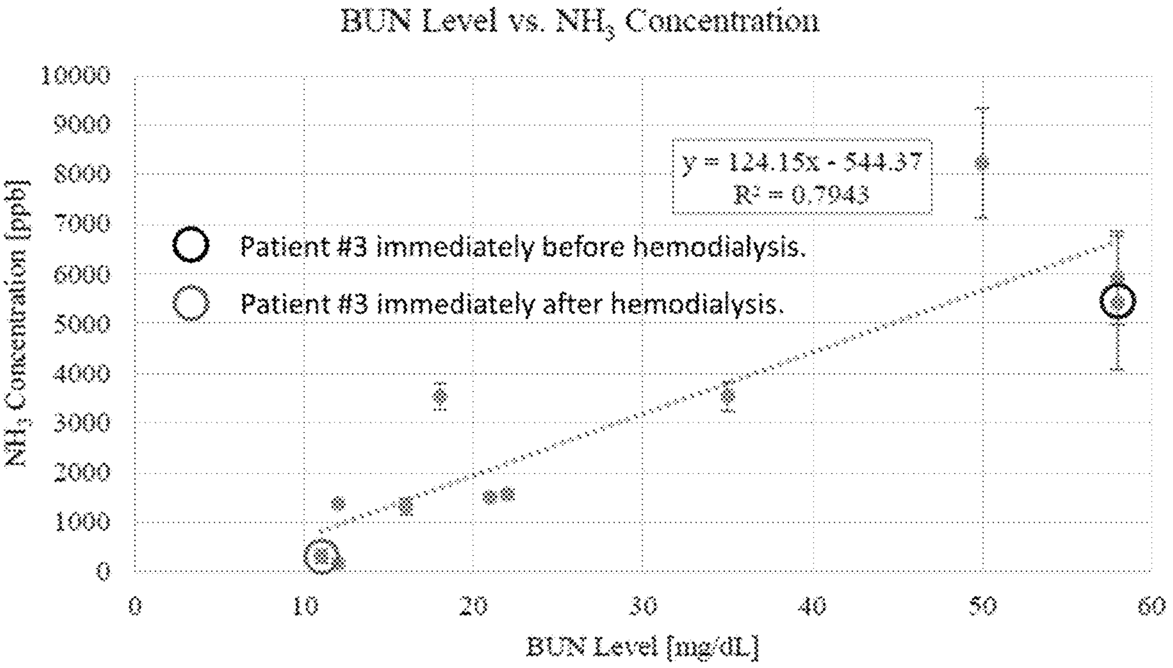
FIG. 11 is a graphical representation of an embodiment of the invention.

The results of patients having various stages of chronic kidney disease was studied. The exhaled-breath test was used by patients exhibiting various stages of chronic kidney disease, thus having different BUN levels, which indicate the degree of urea clearance by the kidneys. Each data point shown in FIG. 11 is for a different patient except for the circled data points. The circled data points are for the same patient immediately before, highest circled data point, and immediately after, lower circled data point, hemodialysis. These data points are particularly important as they then exclude patient-to-patient variation and clearly show that the exhaled-breath test for $NH_3$ is able to respond to BUN levels, which are substantially reduced by hemodialysis to clean urea from the blood stream. Note that the $NH_3$ concentration of the exhaled breath shown on the y-axis in this plot is in units of parts per billion (ppb) while FIGS. 4-6 indicate the $NH_3$ concentration as parts per million (ppm). 1.000 ppm=1,000 ppb. The results are illustrated in FIG. 11 wherein the linear fit is defined by the equation $y=124.15x-544.37$ ($R^2=0.7943$).

The invention has been described with reference to preferred embodiments without limit thereto. One of skill in the art would realize additional embodiments which are described and set forth in the claims appended hereto.

The invention claimed is:

1. An apparatus for measuring ammonia concentration in exhaled breath comprising:
- a mouthpiece and an inlet tube attached to said mouthpiece, wherein said mouthpiece and said inlet tube are capable of capturing exhaled breath;
- a column, said inlet tube positioned at a first end of said column, and
- a colorimetric sensor positioned at a second end of said column, wherein said colorimetric sensor is contained in a bottom cap at said second end of said column, wherein said colorimetric sensor comprises an active component on a substrate, wherein said colorimetric sensor changes color proportional to the ammonia concentration in said exhaled breath, wherein said column comprises an internal cylinder which is within said column, wherein said colorimetric sensor is positioned at an end of said column, wherein said exhaled breath flows from said inlet tube through the internal cylinder into functional contact with the colorimetric sensor and through said column; and
- wherein said internal cylinder has an outlet spaced from a surface of said colorimetric sensor such that said internal cylinder focuses impingement of said exhaled breath onto a central region of said colorimetric sensor.

2. The apparatus for measuring ammonia concentration in exhaled breath of claim 1 further comprising a check valve configured to only allow breath to flow in a direction from the patient into the apparatus.

3. The apparatus for measuring ammonia concentration in exhaled breath of claim 2, wherein said check valve traps the exhaled breath inside the apparatus and inhibits rebreathing of the exhaled breath.

4. The apparatus for measuring ammonia concentration in exhaled breath of claim 1 further comprising a holder capable of securing said colorimetric sensor in flow relationship with said internal cylinder.

5. The apparatus for measuring ammonia concentration in exhaled breath of claim 4 wherein said inlet tube has a larger diameter than a diameter of said internal cylinder.

6. The apparatus for measuring ammonia concentration in exhaled breath of claim 4, wherein said annular-shaped holder is annular-shaped and covers an outer region of said colorimetric sensor and exposes the central region of said colorimetric sensor to said exhaled breath.

7. The apparatus for measuring ammonia concentration in exhaled breath of claim 1 further comprising a side arm and a sample bag, wherein said side arm is configured such that said exhaled breath flows through said column to said sample bag to control the volume of said exhaled breath that flows through the apparatus during a breath test.

8. The apparatus for measuring ammonia concentration in exhaled breath of claim 1 further comprising a pressure gauge that can be used to control the flow rate of exhaled breath.

9. The apparatus for measuring ammonia concentration in exhaled breath of claim 1 wherein said substrate is chromatography paper.

10. The apparatus for measuring ammonia concentration in exhaled breath of claim 1 wherein said active component is selected from the group consisting of Berthelot's reagent, Bromocresol Green, Bromophenol Blue, Bromocresol Purple, Titanium (IV) Oxide, and Hydroquinone.

11. The apparatus for measuring ammonia concentration in exhaled breadth of claim 1, wherein said internal cylinder is perpendicular to a surface of the central region of said colorimetric sensor.

12. The apparatus for measuring ammonia concentration in exhaled breath of claim 1, wherein said internal cylinder comprises a small-diameter internal cylinder that focuses a stream of said exhaled breath onto the central region of said colorimetric sensor.

13. The apparatus for measuring ammonia concentration in exhaled breath of claim 1, wherein, after impinging on the central region of said colorimetric sensor, said exhaled breath is deflected by said colorimetric sensor and flows away from said colorimetric sensor within the column in a direction reverse to a direction of flow of said exhaled breath through said internal cylinder.

* * * * *